United States Patent
Gleich

(10) Patent No.: US 8,712,138 B2
(45) Date of Patent: Apr. 29, 2014

(54) DEVICE AND METHOD FOR GENERATING SOFT TISSUE CONTRAST IMAGES

(75) Inventor: Bernhard Gleich, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 170 days.

(21) Appl. No.: 13/498,595

(22) PCT Filed: Oct. 5, 2010

(86) PCT No.: PCT/IB2010/054486
§ 371 (c)(1),
(2), (4) Date: Mar. 28, 2012

(87) PCT Pub. No.: WO2011/045705
PCT Pub. Date: Apr. 21, 2011

(65) Prior Publication Data
US 2012/0183197 A1    Jul. 19, 2012

(30) Foreign Application Priority Data
Oct. 13, 2009 (EP) .................. 09172883

(51) Int. Cl.
*G06K 9/00*  (2006.01)
(52) U.S. Cl.
USPC ............................................. 382/132
(58) Field of Classification Search
USPC .......................... 382/128–134; 128/920–925;
356/39–49; 600/407–414, 424–426;
345/581–618; 250/455
See application file for complete search history.

(56) References Cited

U.S. PATENT DOCUMENTS

| | | | |
|---|---|---|---|
| 4,850,002 A | 7/1989 | Harding et al. | |
| 4,896,342 A | 1/1990 | Harding | |

(Continued)

FOREIGN PATENT DOCUMENTS

| | | |
|---|---|---|
| EP | 1209956 A1 | 5/2002 |
| EP | 0770257 B1 | 12/2002 |

(Continued)

OTHER PUBLICATIONS

Bridge, B., et al.; Preliminary Experiments with an Automated Three-dimensional Compton Imaging System Using a Weak Barium-133 Source; 1989; British Journal of Non-Destructive Testing; 31(3)134-139.

De Man, B., et al.; An Iterative Maximum-Likelihood Polychromatic Algorithm for CT; 2001; IEEE Trans. on Medical Imaging; 20(10)999-1008.

(Continued)

*Primary Examiner* — Atiba O Fitzpatrick

(57) ABSTRACT

The present invention relates to a device for generating soft tissue contrast images of an area of interest of an examination object (5) comprising soft tissue. The proposed device comprises: an x-ray source unit (2, 3) for emitting one or more pulsed pencil x-ray beams (4), an actuator (8, 9) for actuating said x-ray source unit (2, 3) along and/or around said area of interest to direct said one or more pencil beams (11) onto said area of interest from various directions, an electromagnetic signal receiver (11) for receiving electromagnetic signals from the area of interest resulting from absorption and scatter of x-ray photons within the area of interest, and a signal processor unit (12) for processing said received electromagnetic signals and reconstructing a soft tissue contrast image of the area of interest.

20 Claims, 4 Drawing Sheets

(56) References Cited

U.S. PATENT DOCUMENTS

| | | | |
|---|---|---|---|
| 5,583,908 A * | 12/1996 | Antich et al. | 378/65 |
| RE37,899 E | 11/2002 | Grodzins et al. | |
| 7,514,921 B2 | 4/2009 | Woo et al. | |
| 2002/0131551 A1 * | 9/2002 | Johnson et al. | 378/62 |
| 2004/0136492 A1 | 7/2004 | Sokolov | |
| 2008/0253526 A1 | 10/2008 | Boyden et al. | |
| 2011/0019799 A1 * | 1/2011 | Shedlock | 378/87 |

FOREIGN PATENT DOCUMENTS

| | | |
|---|---|---|
| EP | 1502549 A1 | 2/2005 |
| WO | 2005057467 A2 | 6/2005 |
| WO | 2006051442 A1 | 5/2006 |
| WO | 2007034359 A2 | 3/2007 |
| WO | 2008048780 A1 | 4/2008 |

OTHER PUBLICATIONS

Llopart, X., et al.; First test measurements of 64k pixel readout chip working in single photon counting mode; 2003; Nuclear Instruments and Methods in Physics Research; A509:157-163.

Llopart, X., et al.; Medipix2: a 64-k Pixel Readout Chip with 55-um Square Elements Working in Single Photon Counting Mode; 2002; IEEE Trans. on Nuclear Science; 49(5)2279-2283.

Zhu, P., et al.; X-ray Compton backscattering techniques for process tomography: imaging and characterization of materials; 1996; Meas. Sci. Technol.; 7:281-286.

Boyer, C., et al.; Portable hard x-ray source for nondestructive testing and medical imaging; 1998; Rev. Sci. Instr.; vol. 69; pp. 2524-2530.

Pfeiffer, F., et al.; X-ray phase contrast imaging using a grating interferometer; 2006; Europhysics News; 37(5) 13-15.

* cited by examiner

DEVICE AND METHOD FOR GENERATING SOFT TISSUE CONTRAST IMAGES

FIELD OF THE INVENTION

The present invention relates to a device and a corresponding method for generating soft tissue contrast images of an area of interest of an examination object comprising soft tissue.

BACKGROUND OF THE INVENTION

Computed tomography (CT) generates high-quality images of bone-structures and contrast agent distributions. One of the weak points of CT is, however, the discrimination of soft tissues. Magnetic resonance imaging (MRI) has an excellent soft tissue contrast, but not all patients are allowed to be imaged by an MRI procedure. For instance when the patient has some sort of implants, such as a pacemaker, a patient cannot be imaged by an MRI procedure.

SUMMARY OF THE INVENTION

It is an object of the present invention to provide a device and a corresponding method for generating soft tissue contrast images of an area of interest of an examination object, such as a patient, comprising soft tissue, which can also be applied to patients which cannot be subjected to an MRI procedure.

According to one aspect of the present invention a device is proposed comprising:
- an x-ray source unit for emitting one or more pulsed pencil x-ray beams,
- an actuator for actuating said x-ray source unit along and/or around said area of interest to direct said one or more pencil beams onto said area of interest from various directions,
- an electromagnetic signal receiver for receiving electromagnetic signals from the area of interest resulting from absorption and scatter of x-ray photons within the area of interest, and
- a signal processor unit for processing said received electromagnetic signals and reconstructing a soft tissue contrast image of the area of interest.

According to another aspect of the present invention a corresponding method is proposed as defined in claim 15.

Preferred embodiments of the invention are defined in the dependent claims. It shall be understood that the claimed method has similar and/or identical preferred embodiments as the claimed device and as defined in the dependent claims.

The present invention is based on the idea to exploit the generation of a current due to the momentum of an x-ray pulse for the generation of soft tissue contrast images. Compton diodes, which are x-ray detectors in which current is generated in response to the incidence of x-ray radiation, make use of this effect. The physical principle is similar to the so-called Askaryan effect which is, for instance, used for particle detection in Antarctica. The Askaryan effect is the phenomenon whereby a particle travelling faster than light in a dense radiotransparent medium (such as salt, ice or the lunar regolith) produces a shower of secondary charge particles which contain a charge anisotropy and thus emits a cone of coherent radiation in the radio or microwave part of the electromagnetic spectrum.

To exploit this effect it is proposed according to the present invention to generate short (preferably below 1 μs, or even below <100 ns; preferably below 1 ns, but the limiting factor is the size of the examination object) pulses of intense pencil x-ray beams. These one or more pencil beams penetrate the examination object. In the soft tissue of the object, the photons are mainly absorbed and scattered by the Compton effect. The Compton effect transfers the momentum of the photon (partially) to the electrons. Assuming 1 mJ photons carry the momentum. Depositing the momentum on an absorber having a length of 10 cm, this would ideally correspond to a current of 6 A. If the absorber has a volume of 1 l, a current density of 0.6 mA/mm$^2$ is obtained. Letting the pencil beam move across the complete surface an applied dose of 1 mJ/l=1 mGray is obtained. Hence, a 1 mm pencil beam generates a magnetic field of 1 nT in a distance of 10 cm. For comparison, typical local doses in CT are in the order of 100 mJ/l.

This magnetic field signal is received by an electromagnetic signal receiver, such as a coil or an antenna, for instance a coil similar to the RF coil used in MRI devices for signal reception. These signals are then further processed, and a soft tissue contrast image of the area of interest of the examination object can be reconstructed.

The noise generated by a patient is in the order of <0.1 fT/sqrt(Hz). Averaged over 1 s, this is 7 orders of magnitude lower than the x-ray generated magnetic field. To estimate the total signal to noise ratio, the bandwidth of the electromagnetic signals received by the signal receiver has to be estimated. The inverse resonance frequency quality product of a human is higher than 100 ns, so the current may persist for more than 100 ns. This means that the signal to noise ratio for a single projection could be at least 3000.

To form a soft tissue image, the one or more pencil x-ray beams are scanned over the examination object by an actuator. Preferably, this scanning is performed for different angles like usually done in CT.

There are generally different effects leading to a directed electric current. Apart from the Compton effect, also with the photo effect a magnetic field is generated. The photo effect generally only generates undirected fast electrons which vaporize from the voxel in which they are generated and then have to fall back as electric current. In a homogeneous medium, this does not lead to a measurable field, but a patient comprises edges separating different conductivities and/or absorption constants for fast electrons. By these edges a symmetry is broken and an external magnetic field is generated which can also be measured by the electromagnetic signal receiver.

According to a preferred embodiment a model is used for reconstructing a soft tissue contrast image of the area of interest, said model using as model parameters one or more parameters, which characterize the interaction of photons with tissue within the area of interest to generate electric currents. The electromagnetic signal receiver is adapted to the frequency range of the generated electric currents, and the frequency range is such that the generated electric currents can penetrate the examination object. Preferably, the electromagnetic signal receiver is adapted for receiving electromagnetic signals in at least a frequency range from 50 to 250 MHz, in particular from 10 to 400 MHz, or even up to 1000 MHz (for smaller objects, such as extremities or small animals up to 3 GHz).

The use of a model in the reconstruction is generally known in the art of image reconstruction. A model predicts a plurality of measurement data. By comparison of the predictions of the model and the actual measurement data it is possible to correctly set the model parameters. For this purpose, the parameters of the model are varied until the measurement data and the model parameters equal each other as good as possible. To determine this equalization an error measure is used, such as the Euclidean norm.

According to a preferred embodiment, the signal processor unit is adapted for reconstructing a soft tissue contrast image of the area of interest by use of a model using as model parameters the (complex) conductivity distribution, the x-ray absorption distribution and the efficiency distribution of the efficiency of the absorption and scatter of x-ray photons and of the momentum transfer from x-ray photons to electrons of the area of interest. By optimizing the model parameters using the received electromagnetic signals, one or more soft tissue contrast images of the area of interest can be reconstructed showing the conductivity distribution, the x-ray absorption distribution and/or the efficiency distribution.

As briefly mentioned above, the electromagnetic signal receiver preferably comprises one or more coils, electrodes and/or dipole antennas for arrangement in close proximity or at the examination object during operation. Preferably, for signal reception coils as well as electrodes (e.g. attached to the examination object) are used. The electrodes can be similar to the electrodes used for ECG, whereas coils are similar to the RF receive coils used in MRI. The signal amplifiers are in both cases, however, broadband frequency amplifiers, at least up to 250 MHz, preferably up to 1 GHz.

According to another preferred embodiment, an x-ray detection unit, in particular at least one x-ray detector per pencil x-ray beam, is provided for detecting x-ray signals from x-ray radiation transmitted through the area of interest of the examination object. Hence, according to this embodiment not only electromagnetic signals but also x-ray signals are separately received. The x-ray signals cannot only be used for generating separate x-ray images, but can also be used to optimize the reconstruction of the soft tissue images from the electromagnetic signals, in particular by improving or adapting the model that is preferably used for reconstructing the soft tissue images. In particular, information gained from the measured x-ray signals can be used to improve the model by said one or more model parameters in advance of reconstructing soft tissue images from the electromagnetic signals. Various options exist for such optimizations as are defined in further dependent claims.

For instance, in an embodiment information of the x-ray absorption distribution within the area of interest is obtained from detected x-ray signals, whereas according to another embodiment information of the location of the examination object is obtained from the detected x-ray signals. The latter information is preferably used in the model by setting the conductivity distribution, the x-ray absorption distribution and the efficiency distribution outside the examination object to zero which much reduces the calculation efforts for reconstructing soft tissue images.

According to another embodiment, an information of the location of the electromagnetic signal receiver, in particular of signal receiver elements, with respect to the area of interest is generated and used in the model. All these embodiments finally lead to a reduction of computation time and to an improvement of the signal quality of the soft tissue contrast images.

As the scanning is generally done like in regular CT, a CT image can be generated from the detected x-ray signals. From this CT image, the Compton part of the absorption can be estimated or reconstructed, for instance using an x-ray detection unit comprising one or more energy-resolving x-ray detectors. Therefore, the initial current source distribution is known. If the conductivity distribution in the tissue was known, it is possible to compute the signal at the electromagnetic signal receiver. On the other hand, it is possible to compute the conductivity distribution starting with the measured electromagnetic signals, although the inverse problem is not linear and therefore needs a high computing power. Finally, an image of the tissue conductivity can be generated having a high resolution, as the current sources are small and lie within the imaged region.

To derive Compton-effect related x-ray signals from the x-ray signals received by the x-ray detection unit it is—in addition or alternatively to using one or more energy resolving x-ray detectors—also possible to use a multi-energy (at least dual-energy) x-ray source for alternately emitting x-ray pulses at at least two different energy levels. Compton effect and photon effect have different energy dependencies. Hence, the Compton effect related x-ray signals can be determined using energy-resolving x-ray detectors and/or a multi-energy x-ray source. From the Compton-effect related x-ray signals information of the efficiency distribution of the efficiency of the absorbed and scattered x-ray photons within the area of interest can be generated and used in a model used for reconstructing a soft tissue contrast image of the area of interest.

The x-ray source unit preferably comprises a pulsed x-ray source for emitting pulsed x-ray radiation and a collimator unit arranged between said x-ray source and said examination object for converting said x-ray radiation into said one or more pulsed pencil beams. Generally, x-ray sources can also be used without collimators if they are able to emit one or more pencil beams, such as an x-ray laser. The spatial distance of the separate pencil beams should be as large as possible. If an x-ray detection unit is provided a single detector element is preferably provided for detection of x-ray radiation enabling the reconstruction of a CT image having a high resolution, preferably a higher resolution than the soft tissue contrast image reconstructed from the received electromagnetic signals. As x-ray source, preferably a flash x-ray source such as known from "Portable hard x-ray source for nondestructive testing and medical imaging", Boyer et al., Rev. Sci. Instr., Vol. 69, No. 6, p. 2524-2530, June 1998 is preferably used. But it is also possible to use a laser to generate electrons which can be used for generating intensive directed x-ray pulses.

Preferably, the x-ray source unit is electromagnetically shielded in order to avoid the coupling of HF pulses from the x-ray source unit directly into the electromagnetic signal receiver.

According to another preferred embodiment in which the x-ray source unit comprises a pulsed x-ray source and a collimator unit, the collimator unit comprises one or more controllable collimator elements, each of said collimator elements being provided for allowing a pencil beam to pass through in a first control state and for blocking an incident pencil beam in a second control state, and a collimator control unit for controlling said controllable collimator element. Generally, according to the present invention one or more pencil beams, i.e. a low number of pencil beams, are simultaneously incident on the examination object. This, however, has the disadvantage that a large amount of the x-ray radiation generated by a conventional x-ray source is blocked. However, to enable a reasonable signal to noise ratio, a certain threshold energy has to be introduced into the examination object per x-ray pulse. Hence, according to this preferred embodiment, not only a single or a low number of pencil beams is used but a larger number of pencil beams is made to be incident onto the examination object simultaneously.

For instance, if only a single pencil beam (1 mm×1 mm) is incident onto the examination object, an energy of the electron beam pulse of approximately 100 J is required per pulse.

Since the energy of the pulse has to be released within approximately $10^{-8}$ s, the anode is subjected to a large heating. If, however, a large number of pencil beams are incident simultaneously onto the examination object, a much smaller energy must be deposited onto the anode, which is thus only subjected to less heating.

From the electromagnetic signals, however, essentially the summary information from all current flows is obtained. Therefore, it is preferred to control the switching of the collimator elements of the collimator unit by a collimator control unit. Preferably, in each potential pencil beam path, a collimator element is provided for allowing the radiation along this beam path to pass or being blocked. For this purpose, for instance, a switchable absorber can be used as collimator element, such as an absorber element made from tungsten that can be brought in or out of the beam path. The collimator elements are then switched such that for each pulsed x-ray beam emitted by the x-ray source more than one and, preferably, (less than all) collimator elements, for instance 50% of said collimator elements, are in the second control state in which the respective incident pencil beam is blocked. Thus, according to this embodiment, the emission of the pencil beams is some kind of coded.

If the reconstruction is done using the model (as will be explained in more detail below) no particular changes to the reconstruction have to be made if the collimator elements are switched as explained above. It is, however, also possible to calculate back to single x-rays. For this purpose weighted sums of the voltages of the single projections are formed. The weights must be selected such that the calculated x-ray intensities of all x-rays cancel each other out except for one x-ray. For instance, if the x-ray profiles 00 and 01 are given, an x-ray on the right side can be generated if the second signal is subtracted from the first signal. It is also possible to derive a postulation for the pattern, in particular that they are sufficiently orthogonal so that weighted sums for each x-ray can be found. Otherwise, the pattern is not suitable for imaging and providing a high resolution.

The electrical conductivity reconstruction problem is generally not local. This means, it is preferred to know the tissue conductivity outside the imaging plane or volume. Hence, according to a further embodiment, a larger axial section of the examination object is scanned than generally needed for the diagnosis. As the required resolution is low there, this contributes only little to the applied x-ray dosage. A further reduction of the dose can be obtained if multiple electromagnetic signal receivers, such as multiple receive coils, e.g. in a magnetic induction tomography mode, which is a technique similar to electrical impedance tomography, are used. If multiple electromagnetic signal receivers are used, it is, for instance, possible to use one receiver element as a sender and the other receiver elements as receivers. In this mode a rough image of the conductivity can be reconstructed for further use in the reconstruction of the soft tissue contrast images.

For actuating the x-ray source unit along and/or around the area of interest various options exist. For instance, the actuator may comprise a gantry for rotating the x-ray source unit around the examination object as in a conventional CT apparatus. The actuator may also comprise a translational and pivoting movement means for translational movement of the x-ray source unit along the examination object and for pivoting said x-ray source unit, for instance, as in a conventional tomosynthesis apparatus. However, other structural arrangements can be envisaged for performing the desired function of the actuator.

According to a further embodiment, the device according to the present invention further comprises an acoustic signal receiver, in particular one or more microphones, for arrangement in close proximity or at the examination object during operation for receiving acoustic signals, wherein said signal processor unit is adapted for processing said received acoustic signals for reconstructing a soft tissue contrast image of the area of interest by use of a model using as model parameters the x-ray absorption distribution, thermal expansion, compressibility, density, acoustic velocity and/or acoustic absorption. The pulsed x-ray pencil beams also generate acoustic waves that can be detected. Calculations indicate that the achievable signals to noise ratio is somewhat lower than with the electrical detection. Nevertheless, this generates some signal and adds complementary information to the tissue parameters.

Preferably, broadband microphones are arranged around the examination object. Apart from that, the reconstruction is similar to the reconstruction of the soft tissue images from the electromagnetic signals. The reconstruction delivers images of the source strength (x-ray absorption times thermal expansion divided by volume-related thermal capacity) and the acoustic features of the tissue, acoustic velocity, acoustic absorption and density.

The imaging speech of the method according to the present invention might be lower than in conventional CT but still reasonable. Assuming 10 to 100 J discharge energy from each x-ray pulse, then $1e^4$ pulses per second seem to be reasonable. The signal from each signal receiving element is a time series of many samples. As the signal to noise ratio is high, it is possible to extract several independent pieces of information therefrom. In total, for instance, 160 kilo-voxels per second may be recorded, which is already higher than the speed reached with MRI. Possibly, even higher speeds might be achievable if $1e^6$ pulses per second could be emitted by the x-ray source (which is generally possible if only 100 mJ energy per pulse are required). Then, up to 16 mega-voxels per second could be recorded.

The resolution of the CT image can be higher than the soft tissue image as the pencil beam x-ray photons may be recorded using several detectors. It is also generally possible to broaden the x-ray beams and use the device according to the present invention in a conventional CT mode with fast image acquisition.

The pencil beam like acquisition of the signals allows that CT acquisition virtually without blurring due to scattered radiation. Moreover, the scattered intensity may be recorded, adding information about the tissue, i.e. quantification of photo- and Compton-effect.

Hence, the main advantages of the present invention are that a higher resolution soft tissue contrast image can be generated which adds only negligible extra radiation to the examination. No contrast medium is needed. The device may also be used to deliver high quality classic CT images.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
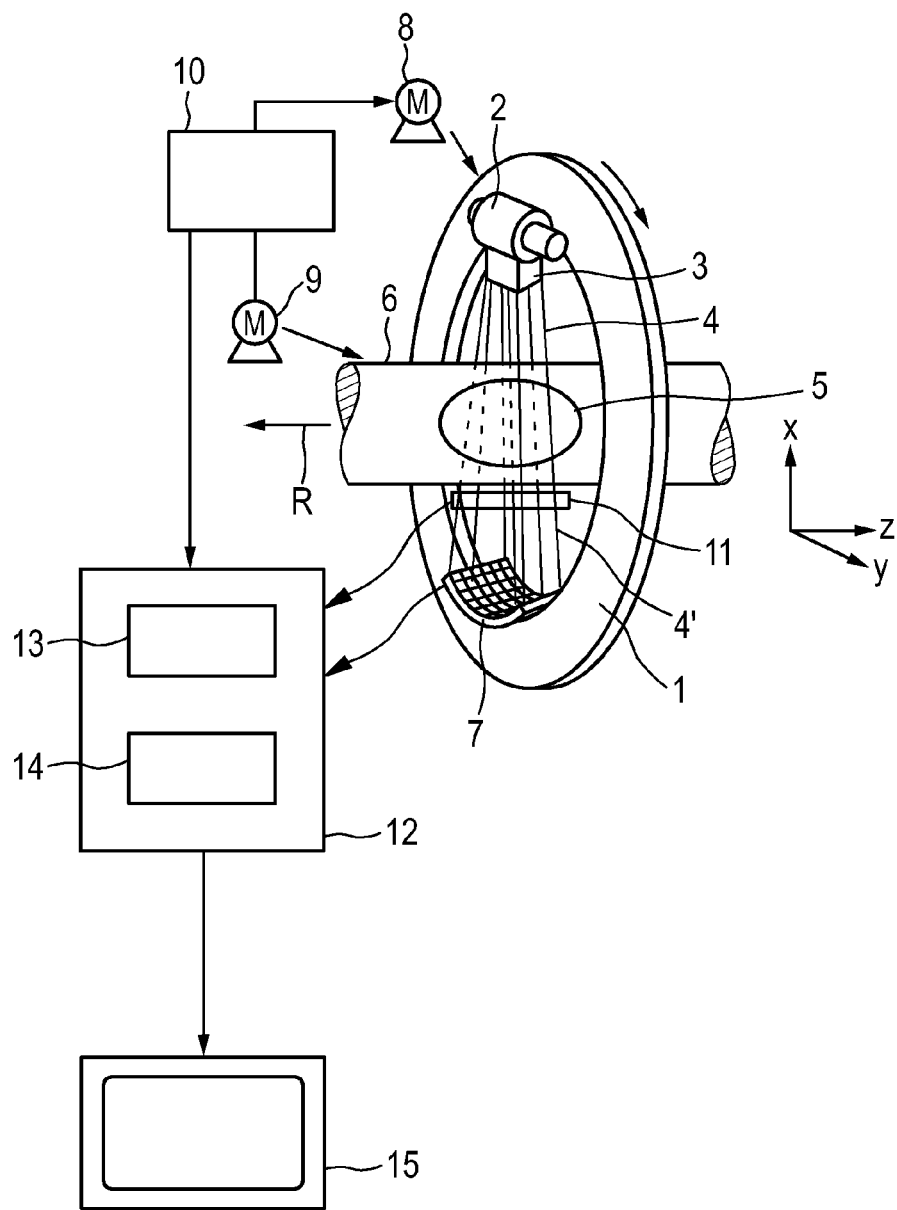
FIG. 1 shows a first embodiment of a device according to the present invention.

FIG. 1 shows a first embodiment of a device according to the present invention. In this embodiment the mechanical layout is similar to a conventional CT imaging device. The device comprises a gantry 1 which is capable of rotating about an axis of rotation R which extends parallel to the z direction. A radiation source unit including an x-ray source 2, such as an x-ray tube, is mounted on the gantry 1. The x-ray source unit further comprises a collimator unit 3 which forms a bundle of pencil beams 4 (at least one pencil beam) from the radiation beam emitted by the x-ray source 2.

The pencil beams traverse a (symbolically shown) object 5, such as a patient, in an area of interest within a cylindrical examination zone 6. After having traversed the examination zone 6, the portion of the x-ray radiation 4' of the pencil beams, that has not been absorbed by the object 5, is incident on an x-ray detector unit 7, in this embodiment a two-dimensional energy-resolving detector, which is also mounted on the gantry 1. Such energy-resolving x-ray detectors work, for example, on the principle of counting the incident photons and output a signal that shows the number of photons per energy in a certain energy area. Such an energy-resolving detector is, for instance, described in Llopart, X., et al. "First test measurements of a 64 k pixel readout chip working in a single photon counting mode", Nucl. Inst, and Meth. A, 509 (1-3): 157-163, 2003 and in Llopart, X., et al., "Medipix2: A 64-k pixel readout chip with 55 mum square elements working in a single photon counting mode", IEEE Trans. Nucl. Sci. 49(5): 2279-2283, 2002. In another embodiment, however, the x-ray detector unit 7 can be a one-dimensional detector, and it must not necessarily be an energy-resolving detector.

The detector unit 7 generates x-ray signals which can then be processed, e.g. to generate a three-dimensional image data set and/or to generate desired x-ray images, e.g. slice images or projection images, of the object 5 as is generally known in the art of CT.

The gantry 1 is driven at a preferably constant but adjustable angular speed by a motor 8. A further motor 9 is provided for displacing the object 5, for example, the patient who is generally arranged on a patient table (not shown) in the examination zone 6, parallel to the direction of the axis of rotation R or the z axis. These motors 8, 9 are controlled by a control unit 10, for instance such that the x-ray source 2 and the collimator unit 3 move relative with respect to the examination zone 6 along a helical trajectory. But it is preferred, that the object 5 or the examination zone 6 is not moved and that the x-ray source 2 and the collimator 3 are rotated, i.e. that the x-ray source 2 and the collimator 3 travel along a circular trajectory relative to the object 5.

According to the present invention, in addition to the x-ray detection unit 7, which is provided in this embodiment but which is not generally an essential element of the present invention and could thus also be left out or switched off, an electromagnetic signal receiver 11 is provided which is only schematically shown in FIG. 1. By this electromagnetic signal receiver 11, electromagnetic signals from the area of interest are received, that result from the absorption and scatter of x-ray photons within the area of the object 5 that is penetrated by x-ray radiation pencil beams 4. As has been explained above in more detail, according to the Compton-effect the momentum of the x-ray photons is transferred to electrons within soft tissue of the object 5 leading to electromagnetic signals that can be measured by the electromagnetic signal receiver 11.

The electromagnetic signal receiver 11 is generally an antenna that is adapted for the reception of electromagnetic signals in the relevant spectrum, in particular in a frequency range from 50 to 250 MHz, particularly from 10 to 400 MHz, preferably up to 1 GHz. While it can also be adapted to receive signals in a larger frequency range, it is not expected generally that essential signal contributions are present outside the given frequency range.

In practice, the electromagnetic signal receiver 11 may comprise one or more coils, such as coils similar to the RF receive coils used in MRI that are arranged on the object's surface or in close proximity to the object 5, and/or electrodes, such as used in ECG, that are attached to the object's surface in close proximity to the area of interest.

If the electromagnetic signal receiver 11, i.e. the one or more receiver elements, are arranged such that they can be hit by x-ray radiation, they should comprise as few elements with high atomic number as possible. In addition they should comprise a low amount of material (e.g. films of Al rather than thick rods of Cu).

For signal processing of the x-ray signals detected by the x-ray detection unit 7 and of the electromagnetic signals received by the electromagnetic signal receiver 11, a signal processing unit 12 is provided. The signal processing unit 12 may comprise one or more processors, a work station and/or a computer running an appropriate software for processing these signals. For instance, in an embodiment a first processor 13 is provided for processing the received electromagnetic signals from the electromagnetic signal receiver 11, and another processor 14 is provided for processing the x-ray signals detected from the x-ray detection unit 7. Of course, if no x-ray detection unit 7 is provided in the device, the respective second processor 14 may be omitted as well.

From the detected electromagnetic signals the first processor 13 may reconstruct a soft tissue contrast image of the area of interest, and from the detected x-ray signals the second processor 14 may generate an x-ray image. These images may then be displayed on a display unit 15 comprising one or more displays and/or display areas for subsequently or simultaneously displaying the images.

For reconstructing a soft tissue contrast image from the received electromagnetic signals, the signal processor 13 preferably uses a model. The use of models is commonly known in the art of image reconstruction from received signals, e.g. as applied in CT or MRI. Generally, the same reconstruction methods and the same methods for defining the model and applying an error measure for refining the model and finally reconstructing the desired image are applied here as well. Hence, as the skilled person is well familiar with the general use of models for reconstructing images from acquired measurement data, such as x-ray signals or MR signals, it is refrained here from explaining all details for reconstructing an image from such measurement data using a model in all details.

The model parameters of the applied model are selected such that they characterize the interaction of photons with tissue within the area of interest to generate electric currents. Preferred model parameters are the conductivity distribution, the x-ray absorption distribution and the efficiency distribution of the efficiency of the absorption and scatter of x-ray photons and of the momentum transfer from x-ray photons to electrons within the area of interest. Generally, without further prior knowledge that could be inserted initially into the model for refining the model before image reconstruction and/or for reducing the number of model parameters to be optimized during the reconstruction, these major model parameters will then be optimized, e.g. by application of an error measure such as the Euclidean norm, until the error measure is below a predefined threshold or until a predefined number of iterations has been performed. Finally, from this optimization the images of the conductivity distribution, the x-ray absorption distribution and/or the efficiency distribution within the area of interest can be reconstructed delivering information without the soft tissue within the area of interest that may be useful for diagnostic purposes alone and/or in addition to other images, such as x-ray images obtained from the x-ray signals, or that may be useful for planning and/or monitoring a medical intervention of the object.

An embodiment of the applied reconstruction shall be explained in the following in more detail. Generally, from the various electromagnetic signal receiver elements (coils, dipole antennas, electrodes) a time-dependent output voltage signal $U_i(t, \ldots)$ is obtained, wherein $i=1 \ldots N$, and being the number of receiver elements. The voltage signal is not only dependent on the time t but also from other experimental conditions as will be described.

First, the electromagnetic model is inserted such that a voltage signal is described as $U_i(t, J(t=0), \Phi, S_i)$. The variables are:

$J(t=0)$ is the current distribution that is effected initially by the x-ray radiation. Due to the finite velocity of light a current distribution is not effected at time 0, but subsequently along the x-ray which, for simplicity's sake, shall be neglected here. In the discrete version of the above equation J is a vector whose components for instance correspond to the voxel positions to be reconstructed (although it is also possible to use another grid).

$\Phi$ is the distribution of the complex conductivity. In the context here, whenever conductivity is mentioned the complex conductivity is generally meant. Outside of the examination object the conductivity is generally not set to zero (but to the value within vacuum where the conductivity solely has an imaginary part). $\Phi$ is also a vector whose values correspond to voxels.

$S_i$ is the sensitivity of the electromagnetic signal receiver. It is the transfer function resulting from the current density and the associated electric field. The sensitivity is particularly determined by the features and the position of the signal receiver.

Calculating $U_i$ is relatively complex. However, there are generally some methods and computer programs (e.g. FEKO) known and available which perform such calculations.

A model for $J(t=0)$ has to be set up. For this purpose, a particular discrete voxel position j is observed. Then, it holds $J_j(t=0)=D_j \times E_j$. $D_j$ is the absorption dose in volume. In the special case here D is generally a three-dimensional vector since it is important from which direction the absorbed photons have been received. Hence, D contains the information how much dose from which mean direction has been absorbed. This is not only the direction of the incident x-ray but also scattered radiation within the object. $E_j$ is the conversion efficiency at the respective location.

Further, the equation for various photon energies has to be set up. E is a model parameter which possibly carries a useful soft tissue contrast. Hence, E is determined during the error minimization. D could also be determined in the same process which, however, seems not to be useful since it can be determined from other more easily accessible parameters, in particular the x-ray flow $F_j$ and the absorption constant $A_j$: $D_j = F_j \times A_j$. Here, $F_j$ is again a three-dimensional vector. Generally, the attenuation is exponential, but the element j is so small that a linearization can be made.

$F_j$ can be calculated if all absorption constants A are known within the tissue. This is some kind of simplification since generally also the likelihood for scatter is required for which the Compton portion in the absorption is important besides its assumed correlation with its conversion efficiency E. If the angular and intensity distribution of the incident x-ray radiation is known, it is possible to calculate the parameter D from the absorption constants A. Such calculations are also generally known, for instance from CT where suitable simulation programs are often used.

During the data acquisition preferably k different x-ray excitations are used to have sufficient data for reconstructing an image. Different pencil beam positions and directions can be used, but also different patterns and directions of a plurality of pencil beams can be used. This will be explained in more detail below.

For the reconstruction, a minimization is now applied for *sum over all i, sum over all k $(U_i(\text{calculated})-U_i(\text{measured}))$+regularization conditions*. The regularization conditions can be something like a postulation for smoothness, if, for instance, neighboring values are differing too much. In this way, the desired soft tissue contrast images can be reconstructed.

The above explanation of the reconstruction enables the skilled person to carry out the reconstruction. More details regarding reconstruction in general and the use of a model and the application of an error minimization is generally known in the art and shall not be provided here.

Figure 2:
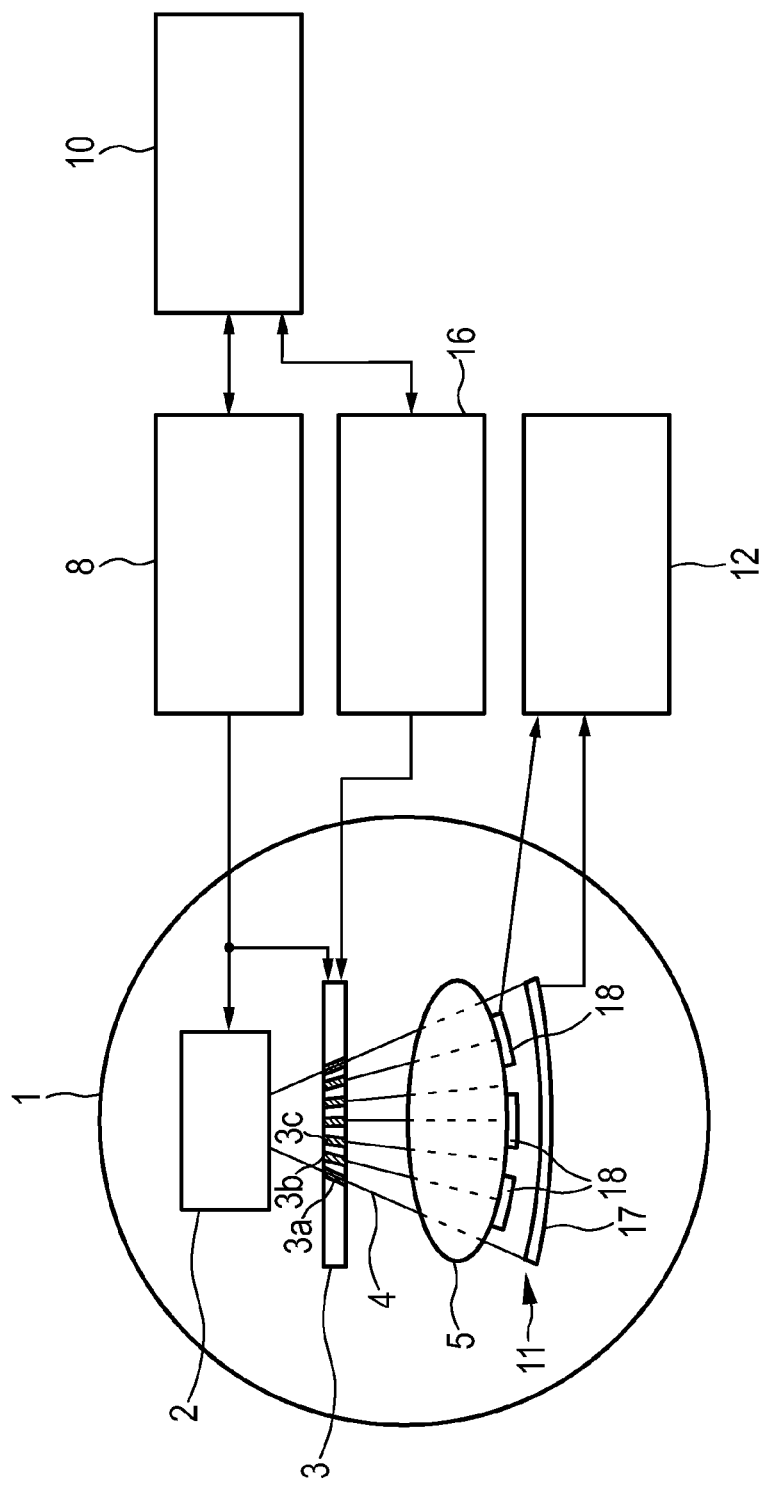
FIG. 2 shows a second embodiment of a device according to the present invention.

Another embodiment of a device according to the present invention is schematically illustrated in FIG. 2. According to this embodiment, the mechanical layout is again similar to the layout of a CT arrangement, i.e. the x-ray source 2 and the collimator 3 are arranged on a gantry 1 and can be rotated around the object 5, e.g. a patient lying on a patient table, by a motor 8. However, in this embodiment no x-ray detection unit is provided, but only an electromagnetic signal receiver 11 which, in this embodiment, may comprise a single body coil 17 arranged below and in close proximity to the object 5 as well as a number of electrodes 18 that are attached to the object's surface. The electromagnetic signals received by the coil 17 and the electrodes 18 are, as explained above, provided to the signal processing unit 12, in particular an electromagnetic signal processor (not shown here) for signal processing, in particular image reconstruction. There may also be a feedback from the signal processing unit 12 to the controller 10, for instance to provide information to the controller 10 from which areas and/or projection angles further data are required so that the controller 10 may control the motor 8 accordingly.

Preferably, in the reconstruction the data from the coil 17 and the electrodes 18, respectively, are commonly used as further measurement data. If the data of these elements are "mixed" in this way it is also possible to perform the reconstruction on the basis of less projections as is generally required for a complete reconstruction of the object. Such techniques for reconstruction are generally known from MR in so-called SENSE (Sensitivity Encoding) applications as, for instance, discussed in various publications of K. Prüssmann et al.

It is, of course, generally also possible to reconstruct images from the data obtained by each single receiver element, which images are then superposed. This, however, generally leads to worse results.

The collimator 3 may simply be an element (as it could be according to the first embodiment), such as a plate, having a number of holes each allowing a pencil beam 4 of the incident x-ray radiation from the x-ray source 2 to pass. According to this second embodiment the collimator 3 comprises a number of collimator elements 3a, 3b, 3c, . . . , that are—separately or in groups—controllable by a collimator control unit 16 which is generally also under control of the controller 10. The collimator elements 3a, 3b, 3c, . . . may be switchable elements that can be switched between a first switching state in which they allow a pencil beam to pass through and a second switching state in which incident radiation is blocked. For this purpose, for instance, switchable absorber elements could be used that can (electronically and/or mechanically) be switched on and off.

According to an embodiment rotatable absorber elements could be used. If the absorber elements are aligned in longitudinal direction x-ray radiation can pass rather well, whereas it is blocked if the absorber elements are in a position orthogonal to the radiation direction. Those absorber elements can be quickly rotated, wherein the frequencies must be slightly different. If the frequencies are correctly set, all desired coding patterns (see below) are subsequently run through. In this way it should be possible to obtain $10^5$ different patterns per second.

According to another embodiment two absorber combs, which are aligned above each other (orthogonal to the radiation direction), could be applied. Such a grating interferometer is, for instance, described in "x-ray phase contrast imaging using a grating interferometer", Pfeiffer F. et al., Europhysics News, No. 5., vol. 37, p. 13-15, 2006. By arranging two of said gratings above each other and moving them, for instance with only 1 m/s with respect to each other, modulations are obtained in the range of MHz. The relative movement of the gratings can, for instance, be achieved by use of piezo elements, magnetostrictive materials and other types of motors.

According to another embodiment, the collimator elements 3a, 3b, 3c, . . . may be implemented by absorber elements, e.g. made of tungsten, that can be moved in and out of a respective hole to block the incident radiation or let it pass. Generally, however, any elements that are at least able to provide these two switching states may be used as collimator elements.

In a simple embodiment all controllable collimator elements 3a, 3b, 3c, . . . are simultaneously controlled, such that they are simultaneously switched on and off to let a bundle of pencil x-ray beams 4 pass or block the incident radiation completely. In a more elaborate embodiment, however, the collimator control unit 16 is adapted for separately controlling the collimator elements 3a, 3b, 3c, . . . separately or in groups.

Using the latter ability, the collimator control unit 16 may control the collimator elements 3a, 3b, 3c, . . . according to a predetermined control pattern that is adapted such that at no time all collimator elements are controlled to be in a control state allowing the radiation to pass through but more than one collimator element is put into such a control state. For instance, a predetermined control pattern could be that at all times 50% of the collimator elements are switched on whereas the other 50% of the collimator elements are switched off. Assuming, just to give an example, eight collimator elements, then a possible control pattern could be (0 meaning that the radiation can pass through and 1 meaning that the radiation is blocked):

11110000
00111100
00001111
11000011
11001100
01100110
00110011
10011001
10101010
01010101

Such a control pattern ensures that the x-ray source, in particular the x-ray anode, is subjected to less heating. The finally measured electromagnetic signal generally is a summary signal of electromagnetic signals generated in a larger area (not just in a small spot-like area) within the object 5. If only a single or a low number of pencil beams for each x-ray pulse is incident onto the object 5, e.g. by use of a structurally fixed collimator having only the respective number of holes, the energy that must be "transported" into the object by this low number of pulses is rather high (because much of the energy is already absorbed before it reaches the object) which may lead to overheating of the anode. Hence, the use of a much larger number of pencil beams that are allowed to pass through the collimator 3 and to hit the object 5, which can be enabled by such a controllable collimator unit 3 as shown in FIG. 2, allows to much reduce the energy that must be "transported" per pencil beam into the object 5 so that the total energy that must be produced by the x-ray source 2 per pulse can also be reduced leading to a reduced heating of the anode. For instance, a total number of 1,000 to 5,000 pencil beams might be useful, whereby other numbers may also be useful, which also depends on the size of the object and/or the area of interest.

Figure 3:
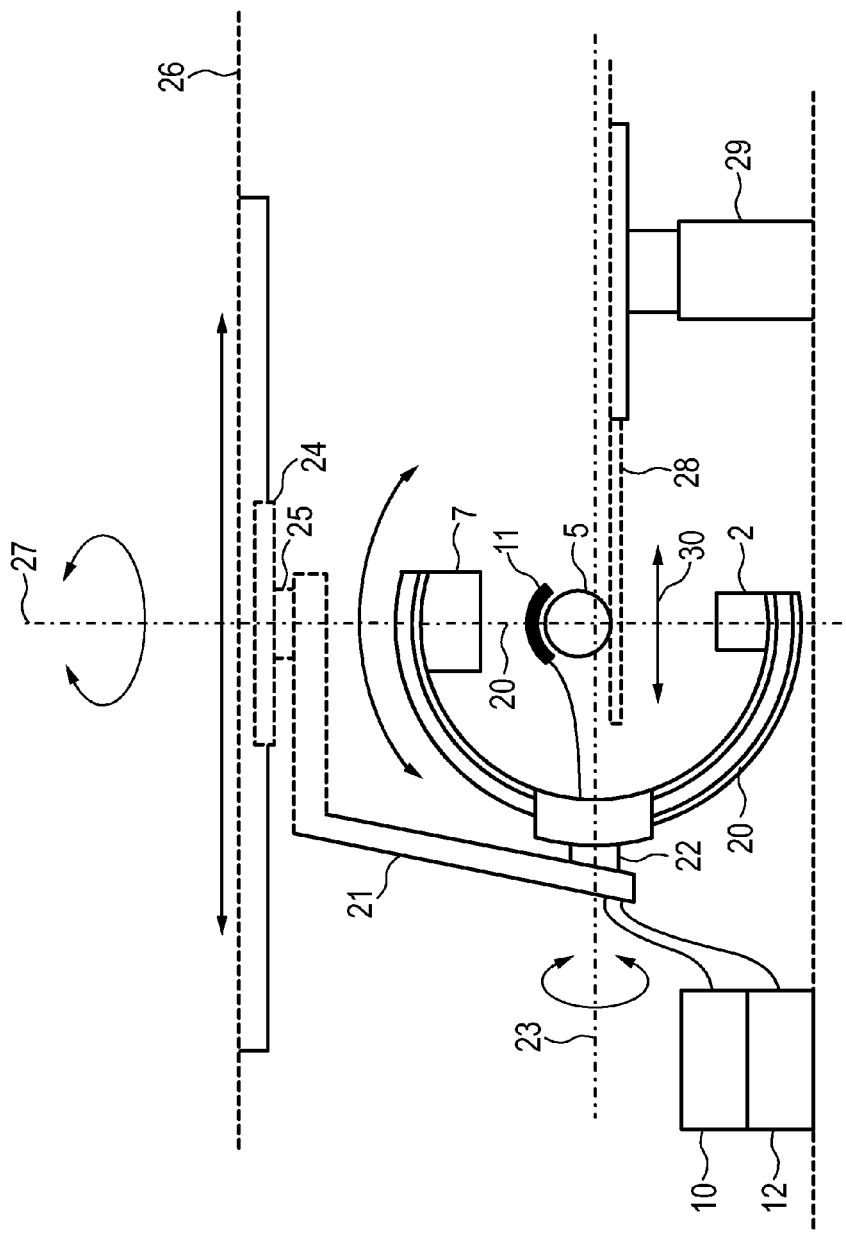
FIG. 3 shows a third embodiment of a device according to the present invention.

FIG. 3 shows a third embodiment of a device according to the present invention. According to this embodiment, the mechanical layout of the device is similar to the layout of an x-ray device applied for tomosynthesis. The device comprises a C-arm 20, the ends of which accommodate the x-ray source 2 and the x-ray detector 7. The C-arm 20 is suspended from an L-arm 21, by way of a pivot 22, so as to be rotatable about the horizontal propeller axis 23. The L-arm 21 is suspended from a displaceable carriage 24 by way of a further pivot 25. Said carriage 24 is suspended from the ceiling 26. The pivot 25 enables rotation about the vertical axis 27. The L-arm 21 can be displaced in the horizontal direction by way of the carriage 24. The object 5 to be examined which is symbolically shown is arranged on a table 28, which is mounted on a base 29 whose height can be adjusted and which is also displaceable in the horizontal direction 30. For acquisition of electromagnetic signals an electromagnetic signal receiver 11 is provided.

The device is controlled by the controller 10 as explained above, and the processing of the acquired signals (electromagnetic signals and x-ray signals) is performed by the signal processing unit 12.

According to this embodiment, the x-ray source 2 and the x-ray detector 7 can thus be moved relative to the object 5 in a translational direction, i.e. in a direction parallel to the patient table 28. Further, pivoting of the x-ray source 2 and the x-ray detection unit 7 with respect to the object 5 is also enabled so that pulsed x-ray pencil beams can be made incident on the object 5 under various angles of incidence.

The electromagnetic signal receiver 11 may thus be made large enough to receive sufficient electromagnetic signal emitted out of the object 5 from whatever direction the area of interest within the object 5 is irradiated. Alternatively, not only a single electromagnetic receiver element, but a plurality of electromagnetic signal receiver elements may be placed on or around the object 5, or the electromagnetic signal receiver 11 may be made moveable such that it is moved similarly as the x-ray source 2 and the x-ray detector 7 in the same direction (e.g. by mechanically coupling the electromagnetic signal receiver 11 to the x-ray detector 7).

Further, according to this embodiment, a flash x-ray source or a laser x-ray source may be used, by which pulsed x-ray pencil beams can be emitted, so that an additional collimator for transforming a (broad) x-ray radiation beam into one or more pencil beams can be omitted. Needless to say that such an x-ray source can also be employed in the other embodiments replacing the x-ray source and the collimator unit there. Similarly, the x-ray sources and collimators explained with respect to the other embodiments can also be used in this embodiment shown in FIG. 3.

If the device according to the present invention comprises, in addition to the electromagnetic signal receiver 11, also an x-ray detection unit 7, as is shown in the embodiments illustrated in FIGS. 1 and 3 (which may generally also be additionally provided in the embodiment shown in FIG. 2), some additional prior information may be gained by which the model, that is preferably used for the reconstruction of soft tissue contrast images from the received electromagnetic signals, can be refined or improved, respectively.

For instance, if in a first step x-ray signals are acquired (preferably with only a low x-ray dosage since only a rough low-resolution x-ray data set is needed) information can be gained about the location of the object 5 within the examination region 6. This information can be used to set the model parameters used for reconstructing soft tissue contrast images outside the object 5 to zero before the model is actually applied for reconstruction.

Further, it may be possible to derive the Compton-effect related x-ray signals from the x-ray signals received by the x-ray detector, particularly if the x-ray detector is an energy-resolving x-ray detector and/or if the x-ray source is a multi-energy x-ray source for alternately emitting x-ray pulses at at least two different energy levels. These Compton-effect related x-ray signals, i.e. the portion of the x-ray signals that are reflecting the Compton part of the absorption, can be exploited by generating information of the efficiency distribution of the efficiency of the absorption and scatter of x-ray photons within the area of interest. This information can then be used as prior information in the model used for reconstructing soft tissue contrast images as a further refinement or improvement of the initial model. By use of such prior information the accuracy and computation time of the reconstruction can thus be improved.

Still further, it may also be possible to generate information of the location of the electromagnetic signal receiver, e.g. from detected x-ray signals and/or from a registration of said signal receivers, which information may then also be used in the model for reconstructing a soft tissue contrast image. For instance, one parameter in the reconstruction is the sensitivity of the electromagnetic signal receiver. If the position (and/or form) of the receiver is exactly known, its sensitivity can be calculated using an electromagnetic model and, hence, no extra parameter has to be introduced in the model used for reconstruction.

Generally, as much as possible prior information will be used in the initial definition or refinement of the model to save computation time and to improve accuracy of the reconstruction of the soft tissue contrast images.

Figure 4:
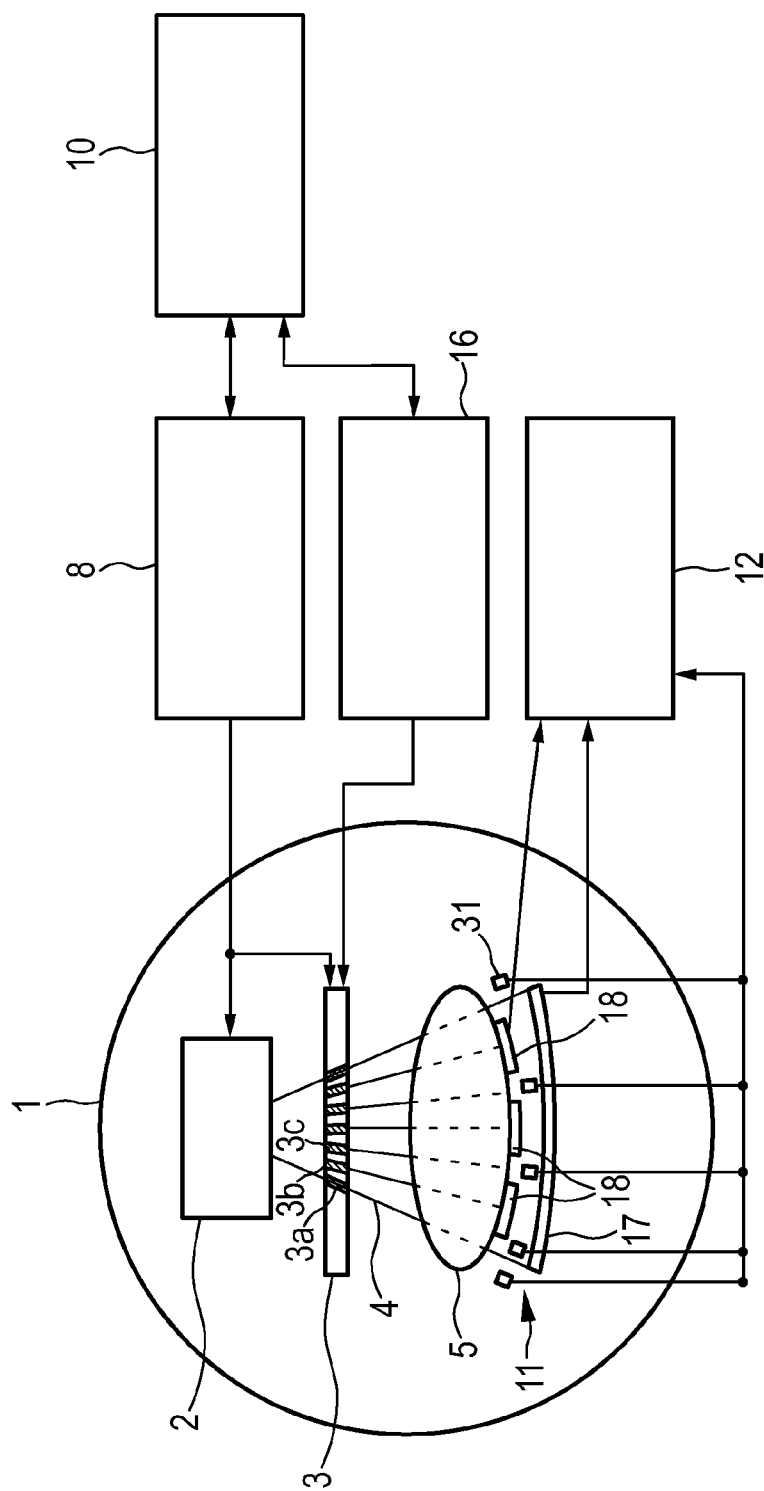
FIG. 4 shows a fourth embodiment of a device according to the present invention.

FIG. 4 schematically shows a fourth embodiment of a device according to the present invention. In addition to the embodiment shown in FIG. 2 this embodiment comprises acoustic signal receivers 31, in particular a plurality of microphones that are arranged close to the object 5. These acoustic signal receivers 31 are adapted for receiving acoustic signals from the object 5.

The tissue is heated when x-ray radiation is incident. Hence, the tissue expands and emits an acoustic pulse which can be measured by the acoustic signal receivers 31. The signal processor unit 12 is, according to this embodiment, adapted for also processing said acoustic signals and for reconstructing a separate soft tissue contrast image of the area of interest within the object 5 by use of an appropriate model, which preferably uses as model parameters the x-ray absorption distribution, thermal expansion, compressibility, density, acoustic velocity and/or acoustic absorption. Hence, some additional information to the tissue parameters may be gained in addition to the information gained from the electromagnetic signals (and, if available, the x-ray signals). In particular, an additional independent soft tissue contrast can be obtained in which possibly other abnormal structures can be identified.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:

1. A device for generating soft tissue contrast images of an area of interest of an examination object comprising soft tissue, said device comprising:
    an x-ray source unit for emitting one or more pulsed pencil x-ray beams,
    an actuator for actuating said x-ray source unit along and/or around said area of interest to direct said one or more pencil beams onto said area of interest from various directions,
    an electromagnetic signal receiver for receiving electromagnetic signals from the area of interest resulting from absorption and scatter of x-ray photons within the area of interest, and
    a signal processor unit for processing said received electromagnetic signals and reconstructing a soft tissue contrast image of the area of interest,
    wherein said signal processor unit is adapted for reconstructing a soft tissue contrast image of the area of interest by use of a model using as model parameters one or more parameters, which characterize the interaction of photons with tissue within the area of interest to generate electric currents.

2. The device as claimed in claim 1,
    wherein said signal processor unit is adapted for reconstructing a soft tissue contrast image of the area of interest by use of a model using as model parameters the conductivity distribution, the x-ray absorption distribution and the efficiency distribution of the efficiency of the absorption and scatter of x-ray photons and of the momentum transfer from x-ray photons to electrons of the area of interest.

3. The device as claimed in claim 1,
wherein said electromagnetic signal receiver is adapted for receiving electromagnetic signals in at least a frequency range from 10 MHz to 1000 MHz.

4. The device as claimed in claim 1,
wherein said electromagnetic signal receiver comprises one or more coils, electrodes and/or dipole antennas for arrangement in close proximity or at the examination object during operation.

5. The device as claimed in claim 1,
further comprising an x-ray detection unit for detecting x-ray signals from x-ray radiation transmitted through the area of interest of the examination object.

6. The device as claimed in claim 5,
wherein said signal processor unit is adapted for generating information of the x-ray absorption distribution within the area of interest from said detected x-ray signals and for using said information of the x-ray absorption distribution in a model used for reconstructing a soft tissue contrast image of the area of interest.

7. The device as claimed in claim 5,
wherein said signal processor unit is adapted for generating information of the location of the examination object from said detected x-ray signals and for using said information of the location of the examination object in a model used for reconstructing a soft tissue contrast image of the area of interest by setting the conductivity distribution, the x-ray absorption distribution and the efficiency distribution outside the examination object to zero.

8. The device as claimed in claim 5,
wherein said x-ray detection unit comprises one or more energy-resolving x-ray detectors, and
wherein said signal processor unit is adapted for deriving Compton-effect related x-ray signals from the x-ray signals received by said one or more energy-resolving x-ray detectors, for generating information of the efficiency distribution of the efficiency of the absorption and scatter of x-ray photons within the area of interest from said detected Compton-effect related x-ray signals and for using said information of the efficiency distribution in a model used for reconstructing a soft tissue contrast image of the area of interest.

9. The device as claimed in claim 5,
wherein said x-ray source unit comprises a multi-energy x-ray source for alternately emitting x-ray pulses at at least two different energy levels, and
wherein said signal processor unit is adapted for deriving Compton-effect related x-ray signals from the x-ray signals received by said x-ray detection unit, for generating information of the efficiency distribution of the efficiency of the absorption and scatter of x-ray photons within the area of interest from said detected Compton-effect related x-ray signals and for using said information of the efficiency distribution in a model used for reconstructing a soft tissue contrast image of the area of interest.

10. The device as claimed in claim 1,
wherein said signal processor unit is adapted for generating information of the location of the electromagnetic signal receiver with respect to the area of interest, and for using said information of the location of the electromagnetic signal receiver in a model used for reconstructing a soft tissue contrast image of the area of interest.

11. The device as claimed in claim 1,
wherein said x-ray source unit comprises a pulsed x-ray source for emitting pulsed x-ray radiation and a collimator unit arranged between said x-ray source and said examination object for converting said x-ray radiation into said one or more pulsed pencil beams.

12. The device as claimed in claim 11,
wherein said collimator unit comprises one or more controllable collimator elements, each of said collimator elements being provided for allowing a pencil beam to pass through in a first control state and for blocking an incident pencil beam in a second control state, and a collimator control unit for controlling said controllable collimator element.

13. The device as claimed in claim 1,
further comprising an acoustic signal receiver for arrangement in close proximity or at the examination object during operation for receiving acoustic signals, wherein said signal processor unit is adapted for processing said received acoustic signals for reconstructing a soft tissue contrast image of the area of interest by use of a model using as model parameters the x-ray absorption distribution, thermal expansion, compressibility, density, acoustic velocity and/or acoustic absorption.

14. A method for generating soft tissue contrast images of an area of interest of an examination object comprising soft tissue, said method comprising the steps of:
emitting one or more pulsed pencil x-ray beams by an x-ray source unit,
actuating said x-ray source unit along and/or around said area of interest to direct said one or more pencil beams onto said area of interest from various directions,
receiving electromagnetic signals from the area of interest resulting from absorption and scatter of x-ray photons within the area of interest,
wherein said electromagnetic signals are in a frequency range from 10 MHz to 1000 MHz,
processing said received electromagnetic signals, and
reconstructing a soft tissue contrast image of the area of interest.

15. A device for generating soft tissue contrast images of an area of interest of an examination object comprising soft tissue, said device comprising:
an x-ray source unit for emitting one or more pulsed pencil x-ray beams,
an actuator for actuating said x-ray source unit along and/or around said area of interest to direct said one or more pencil beams onto said area of interest from various directions,
an electromagnetic signal receiver for receiving electromagnetic signals from the area of interest resulting from absorption and scatter of x-ray photons within the area of interest, and
a signal processor unit for processing said received electromagnetic signals and reconstructing a soft tissue contrast image of the area of interest,
wherein said signal processor unit is adapted for reconstructing a soft tissue contrast image of the area of interest by use of a model using as model parameters the conductivity distribution, the x-ray absorption distribution and the efficiency distribution of the efficiency of the absorption and scatter of x-ray photons and of the momentum transfer from x-ray photons to electrons of the area of interest.

16. A device for generating soft tissue contrast images of an area of interest of an examination object comprising soft tissue, said device comprising:
an x-ray source unit for emitting one or more pulsed pencil x-ray beams, an actuator for actuating said x-ray source unit along and/or around said area of interest to direct said one or more pencil beams onto said area of interest from various directions, an electromagnetic signal receiver for receiving electromagnetic signals from the area of interest resulting from absorption and scatter of x-ray photons within the area of interest, wherein said electromagnetic signal receiver comprises one or more coils, electrodes and/or dipole antennas for arrangement in close proximity or at the examination object during operation, and a signal processor unit for processing said received electromagnetic signals and reconstructing a soft tissue contrast image of the area of interest.

17. A device for generating soft tissue contrast images of an area of interest of an examination object comprising soft tissue, said device comprising:
an x-ray source unit for emitting one or more pulsed pencil x-ray beams,
an actuator for actuating said x-ray source unit along and/or around said area of interest to direct said one or more pencil beams onto said area of interest from various directions,
an electromagnetic signal receiver for receiving electromagnetic signals from the area of interest resulting from absorption and scatter of x-ray photons within the area of interest,
a signal processor unit for processing said received electromagnetic signals and reconstructing a soft tissue contrast image of the area of interest, and
an x-ray detection unit for detecting x-ray signals from x-ray radiation transmitted through the area of interest of the examination object,
wherein said signal processor unit is adapted for generating information of the location of the examination object from said detected x-ray signals and for using said information of the location of the examination object in a model used for reconstructing a soft tissue contrast image of the area of interest by setting the conductivity distribution, the x-ray absorption distribution and the efficiency distribution outside the examination object to zero.

18. A device for generating soft tissue contrast images of an area of interest of an examination object comprising soft tissue, said device comprising:
an x-ray source unit for emitting one or more pulsed pencil x-ray beams,
an actuator for actuating said x-ray source unit along and/or around said area of interest to direct said one or more pencil beams onto said area of interest from various directions,
an electromagnetic signal receiver for receiving electromagnetic signals from the area of interest resulting from absorption and scatter of x-ray photons within the area of interest,
a signal processor unit for processing said received electromagnetic signals and reconstructing a soft tissue contrast image of the area of interest, and
an x-ray detection unit for detecting x-ray signals from x-ray radiation transmitted through the area of interest of the examination object,
wherein said x-ray detection unit comprises one or more energy-resolving x-ray detectors, and
wherein said signal processor unit is adapted for deriving Compton-effect related x-ray signals from the x-ray signals received by said one or more energy-resolving x-ray detectors, for generating information of the efficiency distribution of the efficiency of the absorption and scatter of x-ray photons within the area of interest from said detected Compton-effect related x-ray signals and for using said information of the efficiency distribution in a model used for reconstructing a soft tissue contrast image of the area of interest.

19. A device for generating soft tissue contrast images of an area of interest of an examination object comprising soft tissue, said device comprising:
an x-ray source unit for emitting one or more pulsed pencil x-ray beams,
an actuator for actuating said x-ray source unit along and/or around said area of interest to direct said one or more pencil beams onto said area of interest from various directions,
an electromagnetic signal receiver for receiving electromagnetic signals from the area of interest resulting from absorption and scatter of x-ray photons within the area of interest,
a signal processor unit for processing said received electromagnetic signals and reconstructing a soft tissue contrast image of the area of interest, and
an x-ray detection unit for detecting x-ray signals from x-ray radiation transmitted through the area of interest of the examination object,
wherein said x-ray source unit comprises a multi-energy x-ray source for alternately emitting x-ray pulses at at least two different energy levels, and
wherein said signal processor unit is adapted for deriving Compton-effect related x-ray signals from the x-ray signals received by said x-ray detection unit, for generating information of the efficiency distribution of the efficiency of the absorption and scatter of x-ray photons within the area of interest from said detected Compton-effect related x-ray signals and for using said information of the efficiency distribution in a model used for reconstructing a soft tissue contrast image of the area of interest.

20. The method of claim 14, further comprising:
reconstructing a soft tissue contrast image of the area of interest by use of a model using as model parameters one or more parameters, which characterize the interaction of photons with tissue within the area of interest to generate electric currents.

* * * * *